United States Patent
Jing et al.

(10) Patent No.: US 7,094,260 B2
(45) Date of Patent: Aug. 22, 2006

(54) BIODEGRADABLE COMMON BILE DUCT STENT AND THE METHOD FOR PREPARING THEREOF

(75) Inventors: Xiabin Jing, Changchun (CN); Tongjun Liu, Changchun (CN); Xuesi Chen, Changchun (CN); Shaohui Liu, Changchun (CN); Xiaoyi Xu, Changchun (CN); Xinchao Bian, Changchun (CN); Youzhu Li, Changchun (CN); Kai Zhang, Changchun (CN)

(73) Assignees: Changhun Institute of Applied Chemistry Chinese Academy of Science, Changchun (CN); First Hospital, Jinlin University, Changchun (CN)

( * ) Notice: Subject to any disclaimer, the term of this patent is extended or adjusted under 35 U.S.C. 154(b) by 0 days.

(21) Appl. No.: 10/821,925

(22) Filed: Apr. 12, 2004

(65) Prior Publication Data
US 2005/0010280 A1   Jan. 13, 2005

(30) Foreign Application Priority Data
Jul. 7, 2003   (CN) ................................ 03 1 48595

(51) Int. Cl.
*A61F 2/04* (2006.01)
(52) U.S. Cl. .................................. 623/23.64; 623/1.38
(58) Field of Classification Search ...... 623/1.11–1.48, 623/23.64–23.7, 1.38
See application file for complete search history.

(56) References Cited
U.S. PATENT DOCUMENTS

| | | | | |
|---|---|---|---|---|
| 2,127,903 A | * | 8/1938 | Bowen | 606/154 |
| 5,342,348 A | * | 8/1994 | Kaplan | 604/891.1 |
| 6,132,471 A | * | 10/2000 | Johlin, Jr. | 623/23.64 |
| 6,174,330 B1 | * | 1/2001 | Stinson | 623/1.34 |
| 6,338,739 B1 | * | 1/2002 | Datta et al. | 623/1.15 |
| 2003/0139796 A1 | * | 7/2003 | Sequin et al. | 623/1.12 |
| 2003/0144730 A1 | * | 7/2003 | Datta et al. | 623/1.16 |
| 2003/0149475 A1 | * | 8/2003 | Hyodoh et al. | 623/1.19 |
| 2003/0181973 A1 | * | 9/2003 | Sahota | 623/1.15 |

* cited by examiner

*Primary Examiner*—Suzette J-J Gherbi
(74) *Attorney, Agent, or Firm*—Birch, Stewart, Kolasch & Birch, LLP

(57) ABSTRACT

A biodegradable common bile duct stent and the method for preparing thereof are provided. The stent is made of biodegradable polymeric material with incorporation of X-ray opaque components. The stent adapts to the anatomical shape of the CBD or it can be sutured together with the wall of the bile duct. After placing the stent in the duct, it maintains its position and does not slip. The circular tube of the stent being suitably sized and having multiple ring-shaped protruding rims at the outer wall and/or with larynx structure, leakage and outflow of the bile are thereby prevented. It can be manufactured by a conventional injection-molding or an extrusion-blowing technique. In surgical operation on the bile duct, the stent can replace the T-tube which is conventionally used to support the duct and guide bile drainage. It can reduce the time required for surgical operation and treatment, reduce possible complications and can be degraded and eliminated as the incision heals and the CBD regains its normal functions.

5 Claims, 2 Drawing Sheets

22

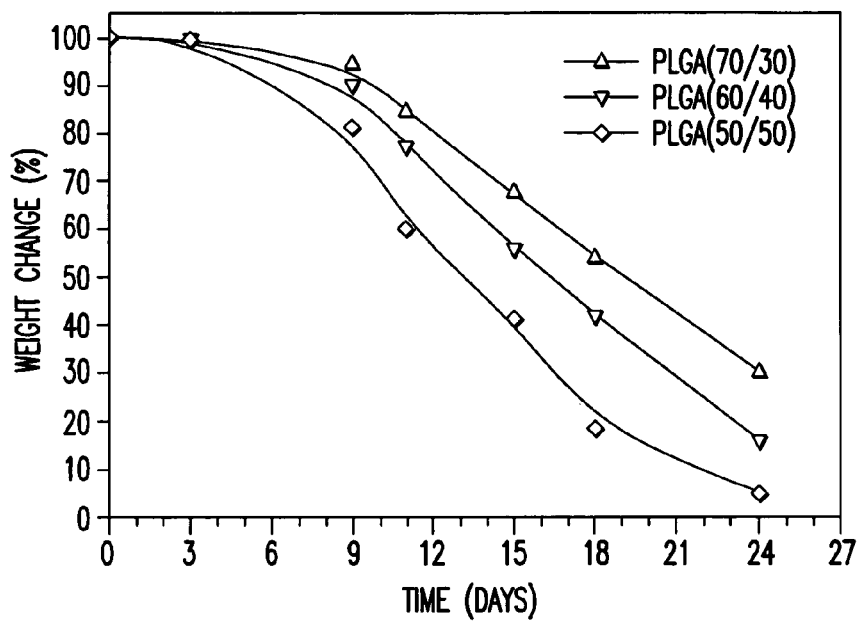
FIG.1
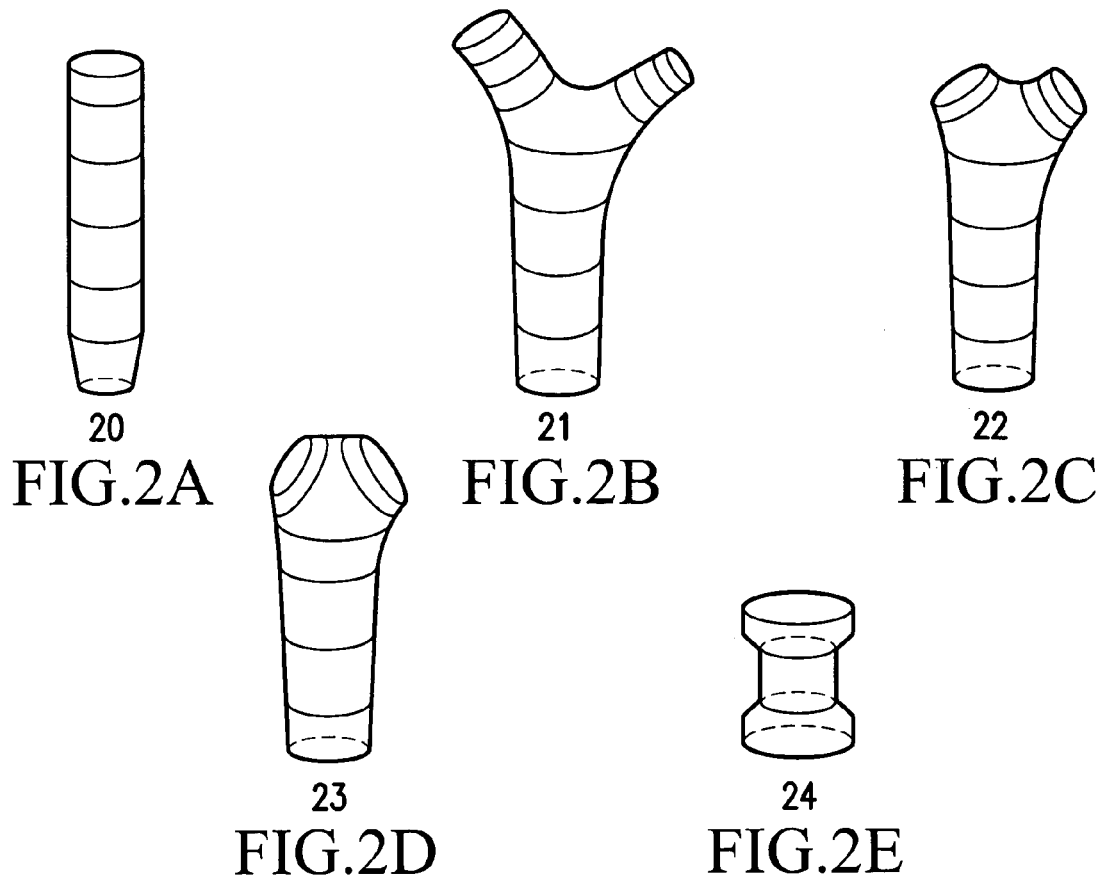
FIG.2A
FIG.2B
FIG.2C
FIG.2D
FIG.2E

BIODEGRADABLE COMMON BILE DUCT STENT AND THE METHOD FOR PREPARING THEREOF

CROSS-REFERENCE TO RELATED APPLICATIONS

This Non-provisional application claims priority under 35 U.S.C. § 119(a) on Patent Application No. 03148595.2 filed in CHINA on Jul. 7, 2003, the entire contents of which are hereby incorporated by reference.

FIELD OF THE INVENTION

The present invention relates to a biodegradable polymeric common bile duct (CBD) stent and its method of preparation.

BACKGROUND OF THE TECHNOLOGY

The common bile duct exploration (CBDE) is a common surgical operation for treating gall-stone, bile duct narrowing and related complaints. In CBDE, a longitudinal incision is made in the common bile duct (CBD) and sutured after the operation. Since simple suturing often includes bile leakage or bile duct narrowing, and thus causes further complications, in clinical practice a T-tube is usually inserted to provide a support during the operation and to keep the bile duct open afterwards. Bile or other secretions can either flow into the intestine through the bile duct or flow out through the long arm of the T-tube fixed in an opening in body wall, thus avoiding complications due to bile duct narrowing or cholestasis. The combination of fitness between the T-tube and the bile duct wall, and the effective suturing will generally prevent the leakage of bile through the incision. The T-tube is removed 2 weeks after the operation, after the sinus formation around the tube.

The insertion of the T-tube may sometimes lead to complications: (1) it may cause an inflamatory reaction, leading to swelling and narrowing of the bile duct; (2) it can induce bile duct infection caused by the counterflow action through its long arm or the infection around the drainage exit at the abdominal wall; (3) if the outflow of bile from the long arm of the T-tube approaches 300–800 ml/day, water-electrolyte disorders and acid-base imbalances occur. This may interfere with the normal mobility of intestine and inhibit the recovery of digestive functions; and (4) if the T-tube is left in position for an extended period it may cause pressure on the surrounding tissues and organs, possibly leading to perforation and adhesion. Furthermore the sinus may not form properly or even break when the T-tube is removed and bile leakage may occur. Alternatives to the T-tube include alternative stent designs such as "C tubes" and the like. All these methods necessitate leaving a stent embedded in the patient's body for about 2 weeks before it is manually removed. In some procedures the stent is inserted through the duodenum, and is moved out from the bile duct into and through the intestine taking advantage of the peristalsis and contraction of the bile duct sphincter. In such procedures it is very difficult to control the time and speed of transfer of the stent to the intestines and the procedure is thus difficult to be adopted clinically.

Liver transplantation is performed to save the patients suffering from serious liver diseases. The operation involves cutting the CBD and suturing the CBD of the donor liver to that of the recipient. The success of liver transplantation depends heavily on the successful joining of the both CBDs. Because of the orientation of cutting and suturing, there is a high risk of bile leakage and bile duct narrowing. Generally a T-tube is required with its associated risks of complications.

The CBD and pancreas duct have a common exit in the duodenum, so some patients need a reconstruction of the common bile duct to perform a pancreatic operation. This is needed to avoid the risk of bile leakage and bile duct narrowing.

SUMMARY OF THE INVENTION

The present invention provides a biodegradable CBD stent, which is made of biodegradable polymeric material with incorporation of X-ray opaque components; the wall of the stent is thin in thickness and continuous, and the diameters of the stent(6–24 mm) are 1–3 times the diameters of CBD in a healthy person(6–8 mm); and the said stent is fabricated according to the anatomic shape of the CBD, and thus is suitable for longitudinal or transverse incisions at each parts of the CBD and common hepatic duct.

The biodegradable stent of the present invention has following fundamental functions:

(1) The stent provides a bolstering for the CBD wall so that it can be conveniently sutured in operation. After the operation it can prevent the occurrence of duct narrowing. The stent also has the function of expanding the bile duct for patients suffering from bile duct narrowing.

(2) The stent can block the incision on the CBD wall and thus avoid the leakage of bile.

(3) The stent can ensure free draining of bile into intestine completely without stasis or running off. Therefore it will not inflict harmful influence on liver functions and will eventually benefit motion of intestines and recovery of digestion functions.

(4) Since the stent does not have drainage side tube, bile duct countercurrent infection and harmful effect on the surrounding tissues caused by the presence of T-tube can be avoided.

(5) After the recovery of the bile duct functions, the stent undergoes biodegradation and the degraded products or fragments will flow into the intestine with the bile. It need not be taken out by a second surgical operation. This will alleviate the suffering of the patients, shorten the hospitalization time and lower the hospitalization expenses.

(6) It can eliminate the inconvenience of body movement and the psychological dread of the patient due to the presence of T-tube in bile duct and can benefit the recovery of patients both physically and emotionally.

The present invention also provides a method for the preparation of biodegradable CBD stent, comprising:

(1) mixing and pelletizing of biodegradable polymer, X-ray opaque components and processing additives;

(2) injection molding or extrusion-blowing into the required shape and size.

The present invention will now be more fully described with reference to Figures which are presented by way of illustration and not limitation. A range of variants such as substitution of other materials or manufacturing methods will be readily apparent to those skilled in the art in light of the following embodiments and the figures and all such variants are considered to fall within the scope of the invention claimed.

DESCRIPTION OF THE FIGURES

FIG. 1: In vitro degradation curves for three types of copolymers of lactic acid and glycollic acid in bile.

FIGS. 2A–2E: Schematic diagrams of the structure of the CBD stent, wherein the Reference Sign 20 is a straight-tube-shaped stent, Reference Sign 21 is a Y-shaped stent, Reference Sign 22 is a short-fork-shaped stent, Reference Sign 23 is a vest-shaped stent, and Reference Sign 24 is a short-tube-shaped stent.

DETAILED DESCRIPTION OF THE EMBODIMENTS OF THE INVENTION

Figure 3A:
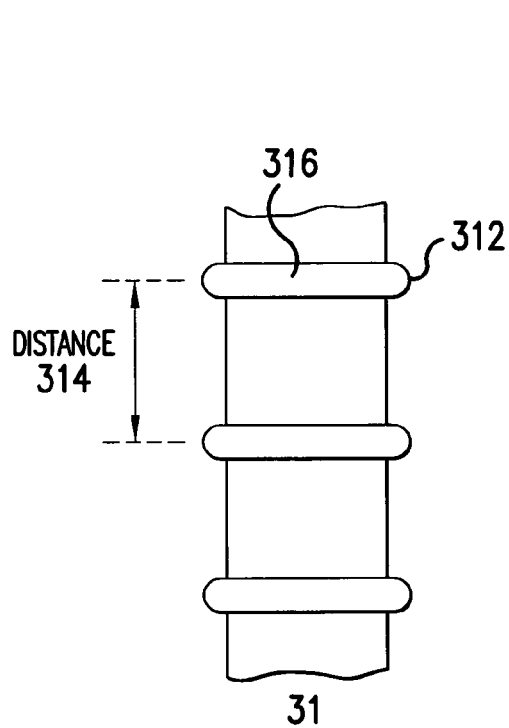
FIGS. 3A and 3B: Schematic diagrams of the wall of the CBD stent, wherein Reference Sign 31 is the ring-shaped diagrams outer wall; Reference Sign 32 is the larynx structure.

The biodegradable CBD stent of the present invention is made of biodegradable polymeric materials. Biodegradable polymers are functional materials developed in the later stage of the 20th century. Their medical uses become wider and wider nowadays, such as suture thread, internal-fixation of bone fracture and the like. The materials have the following characteristics and advantages: After the surgical operation, the stent material undergoes biodegradation and can be absorbed and metabolized by human body and thus there is no need to take the stent out by a second surgical operation. It has been demonstrated by tests that the degradation rate of the lactic acid based polymers is very fast.

FIG. 1 illustrates the weight loss curves of three different polymers during the in vitro degradation in bile. Within 24 days, the weight losses approach 70–100%. In vivo tests show that in about 5 weeks, PLGA (a kind of copolymer formed from lactic acid and glycollic acid) small tube imbedded in CBD of rat can be degraded into fragments and flows into intestine along with the bile. Therefore the use of such kind of material can completely overcome the main disadvantages of T-tube. Since the said stent degrades naturally in body and is not necessary to be taken out by surgical operation or other method, it is called "degradable CBD stent".

In the present invention, the biodegradable polymers used for preparing the CBD stent are selected from the group consisting of a poly(lactic acid), a poly(glycolic acid), a poly($\epsilon$-caprolactone) and a random or block copolymers of lactic acid, a glycolic acid and an $\epsilon$-caprolactone. The steric configuration of poly(lactic acid) could be either laevorotary, dextrorotary or racemic. In the selection of the materials, it is necessary to take account of the velocity of biodegradation, processing properties, post-processing properties, and surface feeling of the product and the like.

Since polymers of lactic acid possess excellent processing property, the shape design of the CBD stent of the present invention could meet the requirements of surgical operation of CBD very well. For example, the stent has a shape selected from the group consisting of a straight tube, a Y-shaped tube, a fork-shaped tube, a vest-shaped tube, and a short tube. The said stent adopts a shape of thin-walled circular tube with outer diameter of 6–25 mm, thickness of the wall in the range of 0.2–2 mm, and length in the range of 10–80 mm. It imitates the anatomic shape of the CBD in appearance.

FIGS. 2A–2E are schematic profiles of the stent structure, wherein Reference Sign 20 is a straight-tube-shaped stent that has the simplest structure, lowest cost and is suitable for incision at the middle or lower part of the CBD; 21 is a Y-shaped stent suitable to be used for a longitudinal or transverse incision at common hepatic duct; 22 is a short-fork-shaped stent; 23 is a vest-shaped stent suitable for longitudinal or transverse incision at CBD; 24 is a short-tube-shaped stent suitable for a transverse incision at common bile(hepatic) duct. The fringe of the stent should be as smooth as possible in order to reduce possible injury to the wall of the bile duct during the operation.

One of the technical difficulties in using an inner-imbedded stent is how to prevent the slip of the stent after operation that would result in blockade of the duct and exposure of the sutured incision. The inner-imbedded stent of the present invention adopts the anatomic shape of the CBD wherein Y-shaped stent 21 has left, right and long arms corresponding to the left, right hepatic ramus duct and CBD respectively. Once implanted, it can stay at the specific place and will not slip. Short-fork-shaped stent 22 and vest-shaped stent 23 have very short left, right arms or have no left, right arms. They can conveniently be imbedded without long incision. Their upper end entrance is relatively wider to facilitate the entering of the bile. The joining part of the three arms is flattened to ensure precise locating in the CBD after the embedment. Short-tube-shaped stent 24 is wider at the two ends and narrower in the middle. Since temporary wall thickening would generally occur at the sutured part of the incision after the operation, the stent will get stuck by such design and will not slip. Straight-tube-shaped stent 20 can not be naturally fixed at a specific position. However since the material used to make the stent is flexible and soft, the stent can be sutured on the wall of the bile duct to fix its position. Of course, stents of other shapes can also be sutured with the wall of the bile duct.

Another technical difficulty in using inner-imbedded stent is how to prevent the leaking of bile from the interstices between the stent and the inner wall of bile duct and then flowing out of the sutured incision. The said stent of the present invention adopts an anatomic shape of the CBD and the outer diameter of the stent is 1–3 times of the CBD of a healthy person. This is due to the fact that patient that needs a surgical operation of CBD often has the symptom of dilatation of CBD and his or her CBD is usually 1–3 times that of a healthy person. This large outer diameter of the stent, especially even larger outer diameter at the upper end, makes the stent tightly adhere to the inner wall of the bile duct without any interstices and therefore leakage of bile can be prevented. As illustrated by 31 in FIG. 3A, the wall has an outer surface comprising multiple protruding rims 312 separated by a distance 314 of between 5 and 10 mm, the cross section 316 of the rims of the rims is in a form of square with round angles, and the width and height of the rims are 1–2 mm, respectively. Their height and shape will not harm the inner wall of the bile duct, but effectively decrease the interstices between the stent and inner wall of the CBD and thus prevent any leakage of bile. The structure, except the protruding part, will exert relatively low tension on the wall of bile duct and will be beneficial to the recovery of functions. The ring-shaped rims themselves have reinforcing effect on the stent and therefore the thickness of the stent wall can suitably be reduced. As a result, the amount of raw material consumed can be lowered and the time required for degradation and excretion can be shortened.

Figure 3B:
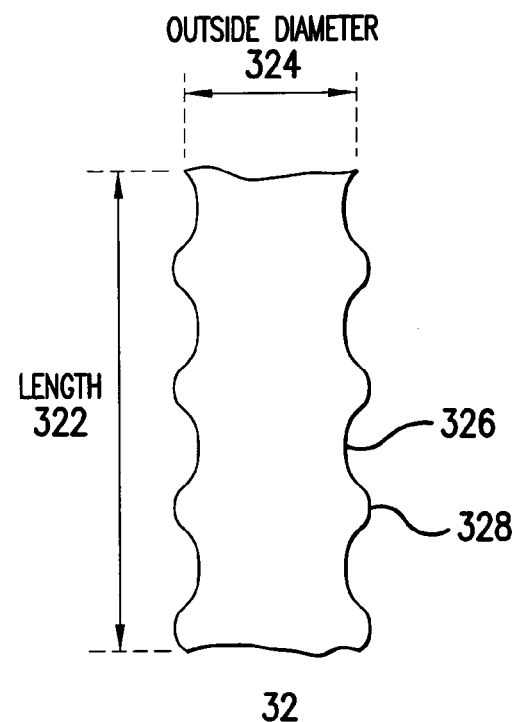

As illustrated by 32 in FIG. 3B, the wall structure of the stent may be fabricated into the shape similar to that of larynx duct. The length of larynx segmentum 322 is 5–20 mm, preferably 8–10 mm; the variation range 324 of outer diameter is 2–10 mm, 4–6 mm; and the width ratio of the concave part 326 and the convex part 328 is 1–10, preferably 3–5. This design will have the same effect of preventing leakage of bile as the multiple ring-shaped protruding rims do. In addition, the design possesses advantages of homogeneity in thickness of the stent wall, easiness of deformation, tight contact with the duct wall and low stress.

Obviously, excellent performances can be obtained if the above-mentioned two structures are utilized together. For example, ring-shaped protruding rims are formed on the left and right arms of the stent (for 21 and 22) and the outer wall of upper entrance (for 23) while larynx duct structure is adopted for the long arm part (for 21, 22, and 23).

In order to conveniently monitor the position, shape and degradation status of the stent after the operation, opaque pigment under X-ray, such as BaSO4 or inorganic salts and oxides of bismuth, tantalum and tungsten is incorporated into the stent. The amount of X-ray opaque components is between 5 and 50% by weight, preferably between 20 and 25% of with respect to the weight based on the weight of the stent. Although addition of X-ray opaque components would cause some changes in the mechanical properties of the polymer, it does not hamper the successful use of the stent. During the degradation of the stent, these compounds may dissociate and flow into the intestine along with the bile and be excreted out of human body.

The manufacturing process for the CBD stent comprises mixing of the raw materials followed by pelletization and molding. Conventional mixer or high-speed mixer is employed in mixing of the raw materials, and screw extruder is employed for pelletization. Injection molding or extrusion-blowing can be used for the fabrication of the stent. If necessary, second molding or post-processing may be used. Those skilled in the art can select suitable process based on those known in prior art.

The above raw materials, structures and method of preparations of the CBD stent will be further described by the following specific examples.

However, the present invention is not limited by these examples. Based on the principles and spirit of the present invention, those skilled in the art can make appropriate improvements or developments on the types of raw materials, structure design and processing techniques.

EXAMPLES

The results of animal experiments are given as follows.

The stent of the present embodiment was made of PLGA copolymer of L-lactide (LA) and glycolide (GA) with a molecular weight of about 120,000 and an LA/GA ratio of 70/30, which was synthesized by the Changchun Institute of Applied Chemistry. The polymer was extruded with a Model XSS-300 extruder (f20 mm, L/D=25) to give thin tubes with an outer diameter of 1.0 mm and an inner diameter of 0.6 mm. The thin tube was cut into stents about 5.5 mm in length and two ends were slightly modified so as to make the ends slightly smaller and smoother in cross-section. The stents made in this way were then sterilized and packed ready for use.

110 Wistar rats are selected and divided into a control group and a test group. Explorations were carried out on the CBDs of the both groups, longitudinal incisions approximately 2 mm long were sutured with 11-0 nylon thread with a 0.4–0.5 mm interval. For control group, the incision was directly sutured after the operation, while for the test group, a stent sterilized with 5% iodine was implanted through the incision after the exploration. The position of the stent was properly adjusted to locate the incision in the middle of the stent and then the incision was sutured.

During the operation, operation time and suturing time were recorded. On the third day after operation, some animals were dissected to observe whether leakage of bile was present. 5 rats were sacrificed to examine the appearance, inner diameter and degradation state of the stents at one week interval. Alkaline phosphatase (ALP) was measured from the blood samples of the rats. 9 weeks after the operation, body weight, outer diameter at the near end of the CBD, ALP and tissue pathology of liver were compared between both groups of rats.

Results: There was no significant difference in the suturing time, total time of operation or percentage of occurrence of cholorrhagia after 3 days between the two groups. After 2 weeks the inner diameter of the stent was slightly expanded; After 3 weeks the stent became deformed but still allowed free drainage; after 4 weeks the stent began to fragmentize and after 5 weeks fragments were excreted out of CBD.

Figure 4:
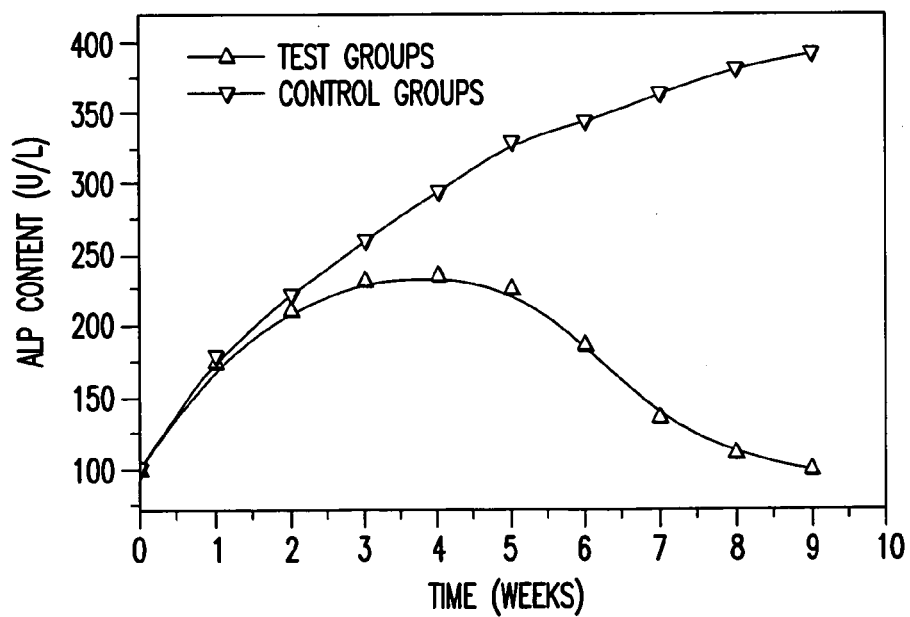
FIG. 4: Post-operation changes in ALP level in rat blood after CBDE and implantation of the CBD stent.

The indexes of ALP value, outer diameter of the near end of the CBD, body weight and injury to the liver for the test group was better than for the control group, which indicates that the degree of bile duct narrowing after the operation was significantly improved by using the CBD stent. Variation of ALP values during the 9 weeks after operation is illustrated in FIG. 4. The ALP index reflects the change in liver function. The value of ALP increases when there is bile duct narrowing and cholestasis. FIG. 4 shows that simple suturing of the CBD resulted in continuous and permanent elevation of ALP level. When the stent was implanted, the observed elevation of ALP level was only temporary and the ALP value would gradually decline, returning to its normal level after 4 weeks.

It should be pointed out that the diameter of the CBD of a rat is about 1 mm and its thickness is about 0.1 mm, much slenderer and thinner than those of the human beings. Therefore, the exploration, implantation and suturing of the CBD for the rat were performed under operating microscope and were much more difficult than the same operation for a human body.

The successful test for the rats indicates that the present invention is clinically applicable based on the materials, stent structure and manufacturing process used in the test as well as considering the dimension and shape of a human CBD.

What is claimed is:

1. A biodegradable common bile duct stent for longitudinal and tranverse incisions at multiple parts of a common bile duct or a common hepatic duct,
   wherein the stent includes a tube structure with thin and continuous walls, and includes an outer shape substantially equal to an anatomical shape of the common bile duct,
   wherein outer diameters of various parts of the stent are substantially equal to 1 to 3 times inner diameters of corresponding parts of the common bile duct of a healthy person,
   wherein the stent is made of biodegradable polymeric material including X-ray opaque components, and
   wherein the said continuous wall of the stent has an outer surface comprising multiple protruding rims separated by a distance of between 5 and 10 mm, wherein the cross section of ring-shaped rims is in a form of square with round angles, and wherein the width and height of the ring-shaped rims are 1–2 mm, respectively.

2. The stent according to claim 1, wherein the stent has a length in the range of 10–80 mm and thickness of the wall in the range of 0.2–2 mm.

3. The stent according to claim 1, wherein the said biodegradable polymers are selected from a group consisting of a poly(lactic acid), a poly(glycolic acid), a poly($\epsilon$-caprolactone) and a random or a block copolymer of lactic acid, a glycolic acid, and an $\epsilon$-caprolactone.

4. The stent according to claim 1, wherein the said X-ray opaque components comprise barium sulfate and inorganic salts or oxides of bismuth, tantalum or tungsten, and an amount of the X-ray opaque components is between 5 and 50% by weight based on a weight of the stent.

5. The stent according to claim 1, wherein the stent is formed by an injection molding process or an extrusion blowing process.

* * * * *